United States Patent [19]

Weissen et al.

[11] Patent Number: 5,543,066
[45] Date of Patent: Aug. 6, 1996

[54] BIODEGRADABLE FABRIC SOFTENING COMPOSITION

[76] Inventors: Hans J. Weissen, Kommweg 4, 52372 Kreuzau; Norbert Porta, Kurfurstenstrasse 20, 52388 Norvenich-Eggerheims, both of Germany

[21] Appl. No.: 283,102

[22] Filed: Jul. 29, 1994

[30] Foreign Application Priority Data

Aug. 10, 1993 [EP] European Pat. Off. ............ 93202352.6

[51] Int. Cl.$^6$ .................................................. D06M 13/46
[52] U.S. Cl. ................. 510/515; 510/519; 510/521; 510/522; 510/525; 510/527
[58] Field of Search ................................. 252/8.6, 8.75, 252/8.8

[56] References Cited

U.S. PATENT DOCUMENTS

| | | | |
|---|---|---|---|
| 4,767,547 | 8/1988 | Straathof et al. ..................... | 252/8.8 |
| 4,923,642 | 5/1990 | Rutzen et al. ........................ | 564/159 |
| 5,066,414 | 11/1991 | Chang ................................. | 252/8.8 |
| 5,399,272 | 3/1995 | Swartley et al. ..................... | 252/8.8 |

FOREIGN PATENT DOCUMENTS

| | | |
|---|---|---|
| 0239910 | 10/1987 | European Pat. Off. . |
| 0550361 | 7/1993 | European Pat. Off. . |
| 59142299 | 2/1983 | Japan . |
| 1571527 | 7/1980 | United Kingdom . |

OTHER PUBLICATIONS

European Search Report issued with respect to priority document: EP 93202352. (Feb. 1994).

*Primary Examiner*—Anthony Green
*Attorney, Agent, or Firm*—Ralph J. Mancini; Louis A. Morris

[57] ABSTRACT

A fabric softening composition containing as essential constituent a biodegradable quaternary ammonium compound, characterized in that the composition comprises at least one or more compounds of the formula:

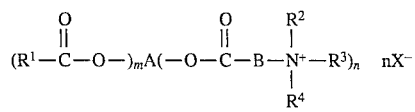

wherein X is an anion, A is an (m+n) valent radical remaining after the removal of (m+n) hydroxy groups from an aliphatic polyol having phydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene or alkylidene group containing 1 to 4 carbon atoms, $R^1$, $R^2$, $R^3$ and $R^4$ are, independently from each other, straight or branched chain C1–C48 alkyl or alkenyl groups, optionally with substitution by one or more functional groups and/or interruption by at most 10 ethylene oxide and/or propylene oxide groups, or by at most two functional groups selected from

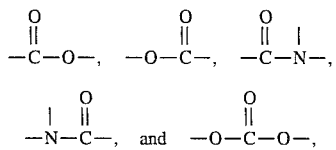

or $R^2$ and $R^3$ may form a ring system containing 5 or 6 atoms in the ring, with the proviso that the average compound either has at least one R group having 22–48 carbon atoms, or at least two R groups having 16–20 carbon atoms, or at least three R groups having 10–14 carbon atoms.

24 Claims, No Drawings

BIODEGRADABLE FABRIC SOFTENING COMPOSITION

FIELD OF INVENTION

The invention generally relates to fabric softening compositions which contain as an essential constituent a biodegradable quaternary ammonium compound.

BACKGROUND OF THE INVENTION

Softening compositions of the above-mentioned type have earlier been suggested in U.S. Pat. No 4 767 547. Preferred among the plurality of compositions described therein are those containing as essential constituent compounds of the formula N,N-di(alkanoyl-oxy-ethyl)-N,N-dimethyl ammonium chloride, their principal representative being, N-di(tallowoyl-oxy-ethyl)-N,N-dimethyl ammonium chloride. However, further improvement of the biodegradability of said compounds was desired, as was further improvement of their toxicity to algae and their suitability to form concentrated dispersions and/or solutions.

The invention now provides fabric softening compositions comprising quaternary ammonium compounds which, by and large, satisfy the above-listed desires.

SUMMARY OF THE INVENTION

The present invention generally relates to fabric softening compositions which contain as an essential constituent, at least one biodegradable quaternary ammonium compound of the formula:

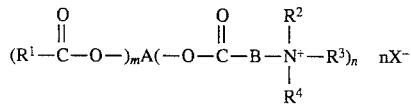

wherein X is an anion, A is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene or alkylidene group containing 1 to 4 carbon atoms, $R^1$, $R^2$, $R^3$ and $R^4$ are, independently from each other, straight or branched chain $C_1$–$C_{48}$ alkyl or alkenyl groups, optionally with substitution by one or more functional groups and/or interruption by at most 10 ethylene oxide and/or propylene oxide groups or by at most two functional groups selected from

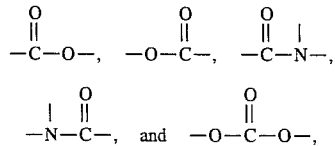

or $R^2$ and $R^3$ may form a ring system containing 5 or 6 atoms in the ring, with the proviso that the average compound either has at least one R group having 22–48 carbon atoms, or at least two R groups having 16–20 carbon atoms, or at least three R groups having 10–14 carbon atoms.

The invention also relates to a method of preparing biodegradable quaternary ammonium compounds of the above-formula.

DETAILED DESCRIPTION OF THE INVENTION

The present invention relates to a fabric softening composition which comprises at least one quaternary ammonium compound of the formula:

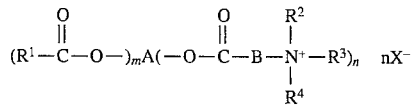

wherein X is an anion, A is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene or alkylidene group containing 1 to 4 carbon atoms, $R^1$, $R^2$, $R^3$ and $R^4$ are independently from each other, straight or branched chain $C_1$–$C_{48}$ alkyl or alkenyl groups, optionally substituted by one or more functional groups and/or interrupted by up to 10 ethylene oxide and/or propylene oxide groups, or by up to two functional groups selected from

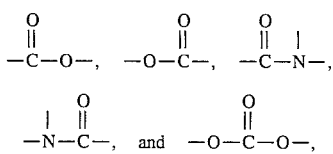

or $R^2$ and $R^3$ may form a ring system containing 5 or 6 atoms in the ring, with the proviso that the average compound either has at least one R group having 22–48 carbon atoms, or at least two R groups having 16–20 carbon atoms, or at least three R groups having 10–14 carbon atoms.

Good results are generally obtained with fabric softening compositions containing as essential constituent a quaternary ammonium compound according to the first mentioned formula in which (m+n) is at least 2.

It should be noted that compounds of a similar structure have already been proposed for use in detergent compositions in U.S. Pat. No. 4 260 529. None of the compounds specifically disclosed therein satisfies the general formula according to the present invention. It should therefore be considered extremely surprising that quaternary ammonium compounds of a structure comparable with that in said U.S. patent specification, but derived from an aliphatic polyol having p hydroxy groups, lead to compositions which not only have good softening properties but also may be applied in a relatively low viscous, highly concentrated form, without the use of any dispersing aids. Under similar circumstances the known quaternary ammonium compounds-containing compositions will become pasty or even solid or tend to gel.

The invention further relates to fabric softening compositions comprising quaternary ammonium compounds according to the first formula obtainable by reaction of:

a) 1 equivalent of an aliphatic polyol having p hydroxy groups, b) m equivalents of an aliphatic carboxylic acid of the formula $R^1$-COOH, and c) n equivalents of a $C_{1-4}$ halocarboxylic acid, followed by treatment with d) n equivalents of a tertiary amine of the formula $R^2R^3R^4N$ or n equivalents of a secondary amine of the formula $R^2R^3NH$, followed by conversion with n equivalents of a quaternizing agent.

The preparation of the present compositions comprising the quaternary ammonium compounds according to the first structural formula can be in the manner known for the preparation of analogous compounds. The quaternization is preferably carried out in the presence of appropriate solvents, e.g., water and/or organic solvents such as low-molecular weight alkanols, e.g., ethanol, isopropanol, diols, e.g., ethyleneglycol, diethyleneglycol, or polyols, e.g., glycerol, or in the presence of the lower alkyl ethers or esters of said compounds, e.g., ethyleneglycol monomethyl ether, diglycolbutyl ether, and/or methoxy polyethyleneglycol.

Within the scope of the invention preference is given to compositions comprising compounds corresponding to the first structural formula obtainable by reaction of a polyol having 2 to 8 hydroxy groups in accordance with the preparative process hereinafter described. Optimum results are obtained when the polyol is selected from the group of ethyleneglycol, glycerol, pentaerythritol, sorbitol, glucose, saccharose, methylglucoside, and/or condensed derivatives thereof. The polyol may be partially etherified and/or esterified. Good results can be obtained when the ester forming derivative of the polyol or the carboxylic acid is a natural fat, preferably a glyceride. Examples of condensed derivatives according to the invention are diglycerol, triglycerol, and dipentaerythritol. Use may also be made of natural polyols such as starch, degraded starch, and oligomers and/or polymers containing repeating units of vinyl alcohol. Compositions comprising compounds corresponding to the first structural formula are obtainable by reaction of an aliphatic carboxylic acid of the formula $R^1$-COOH or an ester thereof in accordance with the preparative process hereinafter described. Optimum results are obtained when said acid is tallow acid and/or at least partially hydrogenated tallow acid. Other examples of suitable quaternary ammonium compounds corresponding to the first structural formula are obtained by replacing tallow acid with, e.g., coconut acid, palmitic acid, lauric acid, oleic acid, stearic acid, or the like.

The $R^2$, $R^3$, and $R^4$ groups are, independently from each other, straight or branched chain $C_1$-$C_{48}$ alkyl or alkenyl groups, optionally with substitution by one or more functional groups and/or interruption by at most 10 ethylene oxide and/or propylene oxide groups, or by at most two functional groups selected from

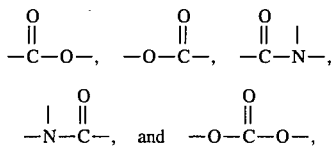

or $R^2$ and $R^3$ may form a ring system containing 5 or 6 atoms in the ring. Typical combinations of $R^2/R^3/R^4$ are: $CH_3/CH_3/CH_3$, $CH_3/CH_3/CH/C_{16/18}$ alk(en)yl, $CH_3/CH_3/CH_2CH_2OOC_{15/17}$ alk(en)yl, $CH_3/CH_3CH_2$ COOC$_{16/18}$ alk(en)yl, $CH_3/CH_3/CH_2CH_2CH_2NHCOC_{15/17}$ alk(en)yl. The $R^2$, $R^3$ and $R^4$ groups can be introduced into the molecule by the use of appropriate tertiary amines such as trimethylamine, (hydrogenated) tallow fatty acid ester of N,N-dimethylethanolamine, (hydrogenated) tallow alcohol ester of N,N-dimethylglycine, (hydrogenated) tallow fatty acid amide of N,N-dimethylaminopropylamine, and dimethyl (hydrogenated) tallowamine. The $R^2$ and $R^3$ groups can also be introduced by the use of appropriate secondary amines such as dimethylamine. The $R^4$ group can then be introduced by quaternization of the thus obtained tertiary amine with halogenating agents such as methylchloride and dimethylsulphate.

If for the preparation of compounds satisfying the first structural formula use is made of a $C_{1-4}$ halocarboxylic acid, preference is given to a monochlorocarboxylic acid, such as 2-chloropropionic acid or 3-chloropropionic acid, optimum results being obtained with monochloroacetic acid.

If use is made of a tertiary amine, preference is given to trimethylamine and dimethylethanolamine esterified with a $C_{10-22}$ carboxylic acid.

Good results may also be obtained when for the tertiary amine use is made of dimethylaminopropylamine amidated with a $C_{10-22}$ carboxylic acid.

All that can be required of the anion X- contained as counterion in the present quaternary ammonium compounds is for it to be compatible with the cationic fabric softening action, to be itself non-toxic, and to generate a water-soluble or water-dispersible salt with the quaternary ammonium cation. Preferably, X - represents a halide anion, more particularly a chloride, sulphate, methosulphate, carboxylate, or sulphonate anion.

The invention further relates to a process for preparing compounds comprising the quaternary ammonium compounds according to the first-mentioned formula, by a) reacting in a first step 1 equivalent of an aliphatic polyol having p free and/or esterified hydroxy groups with m equivalents of an aliphatic acid of the formula $R^1$-COOH or of an ester thereof and n equivalents of a $C_{1-4}$ halocarboxylic acid or of an ester thereof, under reduced pressure at a temperature between 50° and 150° C., followed by either b) heating with n equivalents of a tertiary amine of the formula $R^2R^3R^4N$, optionally in an organic solvent, at a temperature between 40° and 150° C., preferably between 50° and 100° C., or c) heating with n equivalents of a secondary amine of the formula $R^2R^3NH$, optionally in an organic solvent, at a temperature between 40° and 150° C., preferably between 50° and 100° C., followed by conversion with n equivalents of a quaternizing agent, such as methylchloride or dimethylsulphate.

The first reaction step is generally carried out in the presence of a catalyst such as p-toluene sulphonic acid under a reduced pressure of 20-30 mbar and at a temperature of about 60° C. while stripping off the water, followed by an increase in the temperature up to 150° C. over 2-5 hours. The polyol may be partially etherified and/or esterified. Mixtures of polyols are also suitable. If the polyol is glycerol, use may also be made of a mixture of a natural fat and glycerol or another polyol. If use is made of a mixture of a natural fat and a polyol, a preceding transesterification may be carried out under basic conditions, with use being made of a basic catalyst such as sodium methylate or sodium.

During the second reaction step the chlorinated polyol ester is mixed with the desired alkylamine, preferably in appropriate solvents, e.g., water and/or organic solvents such as low-molecular weight alkanols, e.g., ethanol, isopropanol, diols, e.g., ethyleneglycol, diethyleneglycol, or polyols, e.g., glycerol, or in the presence of the lower alkyl ethers or esters of said compounds, e.g., ethyleneglycol monomethyl ether, diglycolbutyl ether, and/or methoxy polyethyleneglycol, followed by heating for 1-2 hours at a temperature between 80° and 100° C. Another process consists in dissolving the chlorinated polyolester in e.g. isopropanol, followed by adding trimethylamine for 10-30 minutes in an autoclave at a pressure <5 bar at an initial temperature of about 50° C. Due to the exothermic reaction, the temperature increases to about 80° C., and the reaction mixture is maintained at said temperature for 0.5-1 hour.

A very attractive process for preparing compounds comprising the quaternary ammonium compounds according to the first formula is characterized by a) reacting in a first step 1 equivalent of an aliphatic polyol having p esterified hydroxy groups with >p moles of dimethyl aminoethanol at a temperature between 80° and 200° C. in the presence of an alkaline catalyst, followed by the distillation of excess dimethyl aminoethanol,
b) esterification in a separate step of an aliphatic, optionally esterified, polyol with at least two moles of chloroacetic acid per mole of polyol, followed by
c) quaternisation of the transesterified tertiary amine obtained in the first reaction step with the esterification product of the second reaction step.

The first reaction step is generally carried out in the presence of an alkaline catalyst such as sodium methylate or sodium. Instead of dimethyl aminoethanol use may also be made of other tertiary amino alcohols such as methyl diethanolamine. The aliphatic polyol preferably is glycerol, which may be wholly or partially esterified with a fatty acid.

The second reaction step is identical with step a) of the process described hereinbefore. For the aliphatic, optionally esterified, polyol use may be made of the by-product of the transesterification reaction of the first step.

The quaternisation reaction of the transesterified tertiary amine obtained in the first reaction step with the chlorinated polyol ester is preferably carried out in appropriate solvents, e.g., water and/or organic solvents such as low-molecular weight alkanols, e.g., ethanol, isopropanol, diols, e.g., ethylene glycol, diethylene glycol, or polyols, e.g., glycerol, or in the presence of the lower alkyl ethers or esters of said compounds, e.g., ethylene glycol monomethyl ether, diglycol butyl ether, and/or methoxy polyethylene glycol, followed by refluxing for 1–2 hours at a temperature between 80° and 100° C.

The fabric softening compositions comprising the quaternary ammonium compounds according to the first structural formula can be used to form dispersions and/or solutions displaying a relatively low viscosity at high concentrations. Non-aqueous solutions may be formed of which 5 up to 90 wt. % of the solids content consists of the compositions according to the invention. Generally, 5 up to 60 wt. % of aqueous solutions consists of the solids content of said compositions, while in the case of aqueous dispersions 5 up to 40 wt. % may consist of the solids content of said compositions.

Tallow is a convenient and inexpensive source of long chain alkyl and alkenyl material. Specific examples of components suitable for preparing the rapidly biodegradable quaternary ammonium compounds according to the invention are given in the Tables below. The components in the first Table comprise a polyol, chloroacetic acid, and a fatty alkyl-containing tertiary amine:

TABLE I

| Polyol | Amine |
|---|---|
| glycerol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| pentaerythritol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |

TABLE I-continued

| Polyol | Amine |
|---|---|
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| diglycerol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| ethyleneglycol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| propyleneglycol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| glucose | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| methyl-α-D-glucopyranoside | N,N-dimethyl-N-(H-tallowyl) |
| methyl-α-D-glucopyranoside | N,N-dimethyl-N-(H-tallowoyl-oxyethyl) |
| methyl-α-D-glucopyranoside | N,N-dimethyl-N-(H-tallowyl-amidopropyl) |
| methyl-α-D-glucopyranoside | N-methyl-N,N-di(H-tallowyl) |
| methyl-α-D-glucopyranoside | 2-(H-tallowyl)-1-(H-tallowoyl-oxyethyl)-4,5-di-hydroimidazole |
| methyl-α-D-glucopyranoside | 2-(H-tallowyl)-1-(H-tallowyl-amidoethyl)-4,5-di-hydroimidazole |
| saccharose | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| sorbitol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |

The components in the following Table comprise a polyol esterified with hydrogenated tallow acid, chloroacetic acid, and a tertiary amine.

TABLE II

| Polyol | Tertiary amine |
|---|---|
| glycerol | N,N-dimethyl-N-(H-tallowyl) |
| " | N,N-dimethyl-N-(H-tallowoyl-oxyethyl) |

TABLE II-continued

| Polyol | Tertiary amine |
|---|---|
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| pentaerythritol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| diglycerol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| ethyleneglycol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| propyleneglycol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| glucose | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| methyl-a-D-glucopyranoside | N,N-dimethyl-N-(H-tallowyl) |
| methyl-a-D-glucopyranoside | N,N-dimethyl-N-(H-tallowoyl-oxyethyl) |
| methyl-a-D-glucopyranoside | N,N-dimethyl-N-(H-tallowyl-amidopropyl) |
| methyl-a-D-glucopyranoside | N,N,N-trimethyl |
| methyl-a-D-glucopyranoside | N,N,N-triethyl |
| methyl-a-D-glucopyranoside | N,N-dimethyl-N-(hydroxyethyl) |
| methyl-a-D-glucopyranoside | N-methyl-N,N-di(H-tallowyl) |
| methyl-a-D-glucopyranoside | 2-(H-tallowyl)-1-(H-tallowoyl-oxyethyl)-4,5-di-hydroimidazole |
| methyl-a-D-glucopyranoside | 2-(H-tallowyl)-1-(H-tallowyl-amidoethyl)-4,5-di-hydroimidazole |
| saccharose | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |
| sorbitol | N,N-dimethyl-N-(H-tallowyl) |
| " | N,N-dimethyl-N-(H-tallowoyl-oxyethyl) |
| " | N,N-dimethyl-N-(H-tallowyl-amidopropyl) |
| " | N,N,N-trimethyl |
| " | N,N,N-triethyl |
| " | N,N-dimethyl-N-(hydroxyethyl) |
| " | N-methyl-N,N-di(H-tallowyl) |
| " | 2-(H-tallowyl)-1-(H-tallowoyl-oxyethyl)-4,5-di-hydroimidazole |
| " | 2-(H-tallowyl)-1-(H-tallowyl-amidoethyl)-4,5-di-hydroimidazole |

In the above examples the hydrogenated tallow residue may be replaced by a fatty alkyl derived from other natural sources such as tallow oil, coconut oil, palmitic oil, and rape oil, all of which may be saturated or unsaturated.

Typical fabric softening compositions according to the present invention include the following quaternary ammonium compounds:

(H-tallowbetaine) glycerol ester bis (H-tallowbetaine) glycerol ester tris (H-tallowbetaine) glycerol ester (H-tallowbetaine) H-tallowoyl glycerol ester bis (H-tallowbetaine) H-tallowoyl glycerol ester betaine di-(H-tallowoyl) glycerol ester di betaine H-tallowoyl glycerol ester (H-tallowbetaine) pentaerythritol ester bis (H-tallowbetaine) pentaerythritol ester tris (H-tallowbetaine) pentaerythritol ester tetra (H-tallowbetaine) pentaerythritol ester (H-tallowbetaine) H-tallowoyl pentaerythritol ester bis (H-tallowbetaine) H-tallowoyl pentaerythritol ester tris (H-tallowbetaine) H-tallowoyl pentaerythritol ester betaine di- (H-tallowoyl) pentaerythritol ester di betaine H-tallowoyl pentaerythritol ester (H-tallowbetaine) diglycerol ester bis (H-tallowbetaine) diglycerol ester tris (H-tallowbetaine) diglycerol ester tetra (H-tallowbetaine) diglycerol ester (H-tallowbetaine) H-tallowoyl diglycerol ester bis (H-tallowbetaine) H-tallowoyl diglycerol ester tris (H-tallowbetaine) H-tallowoyl diglycerol ester betaine di-(H-tallowoyl) diglycerol ester di betaine H-tallowoyl diglycerol ester (H-tallowbetaine) ethyleneglycol ester bis (H-tallowbetaine) ethyleneglycol ester (H-tallowbetaine) H-tallowoyl ethyleneglycol ester (H-tallowbetaine) propyleneglycol ester bis (H-tallowbetaine) propyleneglycol ester (H-tallowbetaine) H-tallowoyl propyleneglycol ester (H-tallowbetaine) glucose ester bis (H-tallowbetaine) glucose ester tris (H-tallowbetaine) glucose ester tetra (H-tallowbetaine) glucose ester (H-tallowbetaine) H-tallowoyl glucose ester bis (H-tallowbetaine) H-tallowoyl glucose ester tris (H-tallowbetaine) H-tallowoyl glucose ester betaine di-(H-tallowoyl) glucose ester di betaine H-tallowoyl glucose ester (H-tallowbetaine) methyl-α-D-glucopyranoside ester bis (H-tallowbetaine) methyl-α-D-glucopyranoside ester tris (H-tallowbetaine) methyl-α-D-glucopyranoside ester tetra (H-tallowbetaine) methyl-α-D-glucopyranoside ester (H-tallowbetaine) H-tallowoyl methyl-α-D-glucopyranoside ester bis (H-tallowbetaine) H-tallowoyl methyl-α-D-glucopyranoside ester tris (H-tallowbetaine) H-tallowoyl methyl-α-D-glucopyranoside ester betaine di-(H-tallowoyl) methyl-α-D-glucopyranoside ester di betaine H-tallowoyl methyl-α-D-glucopyranoside ester (H-tallowbetaine) saccharose ester bis (H-tallowbetaine) saccharose ester tris (H-tallowbetaine) saccharose ester tetra (H-tallowbetaine) saccharose ester (H-tallowbetaine) H-tallowoyl saccharose ester bis (H-tallowbetaine) H-tallowoyl saccharose ester tris (H-tallowbetaine) H-tallowoyl saccharose ester betaine di-(H-tallowoyl) saccharose ester di betaine H-tallowoyl saccharose ester (H-tallowbetaine) sorbitol ester bis (H-tallowbetaine) sorbitol ester tris (H-tallowbetaine) sorbitol ester tetra (H-tallowbetaine) sorbitol ester (H-tallowbetaine) H-tallowoyl sorbitol ester bis (H-tallowbetaine) H-tallowoyl sorbitol ester tris (H-tallowbetaine) H-tallowoyl sorbitol ester betaine di-(H-tallowoyl) sorbitol ester di betaine H-tallowoyl sorbitol ester Preferred compounds of this group are:

bis (H-tallowbetaine) glycerol ester (H-tallowbetaine) H-tallowoyl glycerol ester betaine di-(H-tallowoyl) glycerol ester bis (H-tallowbetaine) pentaerythritol ester (H-tallowbetaine) H-tallowoyl pentaerythritol ester betaine di-(H-tallowoyl) pentaerythritol ester bis (H-tallowbetaine) diglycerol ester (H-tallowbetaine) H-tallowoyl diglycerol ester betaine di-(H-tallowoyl) diglycerol ester bis (H-tallowbetaine) ethyleneglycol ester (H-tallowbetaine) H-tallowoyl ethyleneglycol ester bis (H-tallowbetaine) propyleneglycol ester (H-tallowbetaine) H-tallowoyl propyleneglycol ester bis (H-tallowbetaine) glucose ester (H-tallowbetaine) H-tallowoyl glucose ester betaine di-(H-tallowoyl) glucose ester bis (H-tallowbetaine) methyl-α-D-glucopyranoside ester (H-tallowbetaine) H-tallowoyl methyl-α-D-glucopyranoside ester betaine di-(H-tallowoyl) methyl-α-D-glucopyranoside ester bis (H-tallowbetaine) saccharose ester (H-tallowbetaine) H-tallowoyl saccharose ester betaine di-(H-tallowoyl) saccharose ester bis (H-tallowbetaine) sorbitol ester (H-tallowbetaine) H-tallowoyl sorbitol ester betaine di-(H-tallowoyl) sorbitol ester The compositions optionally contain non-ionics. Such non-ionics comprise polyethyleneglycol, polypropyleneglycol, polyethylene/polypropylene-copolymers, ethoxylated and/or propoxylated lower alkyl amines or polyamines, ethoxylated and/or propoxylated fatty acids, partially esterified polyols, fatty acid alkanolamides, fatty alcohols or fatty amines.

The stability of the compositions can be improved further, and their viscosity adjusted, by the incorporation of small amounts of electrolyte. Examples of suitable electrolytes are the salts of lithium, sodium, potassium, magnesium chloride, calcium chloride, or aluminium chloride and quaternary (lower alkyl) ammonium salts. Optionally, the compositions according to the invention may also comprise acids. Suitable acids are hydrochloric acid, boric acid, and phosphoric acid, or organic acids, such as glycolic acid, citric acid, and tartaric acid.

If the compositions are wholly or partially in the form of dispersions, they may optionally contain dispersion stabilizers. Such stabilizers include ethoxylated fatty alcohols and amines, preferably C10–20 fatty alcohols ethoxylated with 5 to 100 moles of ethylene oxide (e.g., ELFAPUR T250® (talloweth-25) commercially available from Akzo Chemicals) and C10–20 fatty amines ethoxylated with 5 to 100 moles of ethylene oxide (e.g., ETHOMEEN®HT60 (PEG-50 H-tallow amine) commercially available from Akzo Chemicals).

The compositions may optionally contain other ingredients known to be suitable for use in textile softeners. Such adjuvants include perfumes, preservatives, germicides, colorants, dyes, fungicides, brighteners, and opacifiers. These adjuvants, if used, are normally added at their conventional levels. However, in the case of composition ingredients utilized for a fabric treatment effect, e.g., perfumes, these materials can be added at higher than normal levels, corresponding to the degree of concentration of the product.

The invention will be further described in the following examples, which must not be construed as limiting the scope of the present invention.

The manner in which the present biodegradable fabric softening agent is applied is the same as for the conventional, now commercially available fabric softeners, where the agent, together with the surfactant, can be contacted with the textile material to be softened in the form of a rinsing agent or else in the dryer. The fabric softening action envisaged and actualized here is the same as that of the conventional fabric softeners. Inevitably, via the rinsing solution a portion of the fabric softener will end up in the waste water, where, because of the present invention, there will be less harm to the environment as a result of accelerated biodegradability.

DESCRIPTION OF THE TEST METHODS USED

1. Softening

The present quaternary ammonium compounds were tested for their fabric softening performance in a panel test. In the test prewashed terry towels treated with the fabric softeners were line dried for 24 hours and then cut up into strips of 10*20 cm~.

A test panel evaluated the softening action as compared with that of three standards, whereupon the observational data was statistically processed in accordance with DIN standard 10954.

Standards:

1: dimethyl-di-(H-tallow) ammonium chloride (ARQUAD® 2HT) (commercially available from Akzo Chemicals)

2: 1-methyl-2-tallowalkyl-3-tallowamido-ethyl imidazolinium methosulphate (REWOQUAT® 7500 )

3: WMP—test detergent

The ranking of the standards is:

ARQUAD® 2HT>REWOQUAT® 7500>>WMP-test detergent

2. Biodegradation

The present quaternary ammonium compounds were tested for biodegradability in accordance with the EEC/OECD guidelines OECD 301D "closed bottle test". In this experiment a test compound is added to an aqueous solution of mineral salts and exposed for 28 days under aerobic conditions to a relatively small number of micro-organisms. The formal test regulations were departed from on the following minor issues:

the inoculum was taken from an apparatus containing activated sludge preconditioned in accordance with proposed amendments to the EEC guidelines.

ammonium chloride was not included in the medium to avoid nitrification.

The dissolved oxygen concentrations were determined electrochemically using an oxygen electrode (WTW Trioxmatic EO 200) and an oxygen gauge (WTW OXI 530), and biodegradability was calculated as the ratio of biological oxygen demand (BOD) to theoretical oxygen demand (ThOD):

Biodegradability=BOD/ThOD

3. Algae toxicity

The present quaternary ammonium compounds were tested for chronic algae toxicity in accordance with the EEC/OECD guidelines OECD 201 "Alga growth inhibition test". Exponentially-growing cultures of selected green algae (Selenastrum capricornutum ATCC 22662) are exposed to various concentrations of the test substance over several generations under defined conditions. The inhibition of growth in relation to a control culture is determined over a fixed period.

4. Viscosity

Brookfield LVTD, 60 rpm, 20° C., spindle 1.4.

EXAMPLE 1

Preparation of (H-tallow betaine) glycerol esterquats 1 mole of glycerol was esterified with 2 moles of chloroacetic acid at a temperature not exceeding 130° C. The resulting glycerol ester was treated with 2 moles of N,N-dimethyl-N-(H-tallow) amine (ARMEEN® DMHTD) in isopropanol under reflux for 2 hours. The resulting glycerol esterquat was a mixture of the mono-, di-, and triquaternary ammonium compounds.

Properties:

The glycerol esterquat was soluble in water. Surprisingly, it was found that the softening performance was equal to that of REWOQUAT® 7500 despite its solubility in water. A 5% clear, low viscous solution in water could be formed.

EXAMPLE 2

Preparation of (H-tallow betaine) H-tallowoyl glycerol esterquats 1 mole of glycerol was esterified simultaneously with 1 mole of hydrogenated tallow fatty acid and 1.5 moles of chloroacetic acid at a temperature not exceeding 130° C. The resulting glycerol ester was treated with 1.5 moles of N,N-dimethyl-N-(H-tallow)amine (ARMEEN® DMHTD) in isopropanol under reflux for 2 hours. The resulting glycerol esterquat was a mixture of non-ionic glycerol esters and mono-, di-, and triquaternary ammonium compounds.

When the resulting esterquat was dispersed in water, it surprisingly was found that a highly concentrated dispersion of up to 25% by weight could be prepared without making use of any adjuvants.

Softening performance: ARQUAD® 2HT=Example 2>REWOQUAT® W7500>>WMP—test detergent Surprisingly, it was found that despite the content of non-ionics, the softening performance of this esterquat was comparable with that of ARQUAD® 2HT and superior to that of REWOQUAT® W7500.

EXAMPLE 3

Preparation of H-tallowoyl pentaerythritol betaine esterquats 1 mole of pentaerythritol was esterified simultaneously with 2 moles of hydrogenated tallow fatty acid and 1.5 moles of chloroacetic acid at a temperature not exceeding 150° C. The resulting pentaerythritol ester was treated with 1.5 moles of trimethylamine in isopropanol in an autoclave at 80° C. and a pressure of 2 bar for 2 hours. The resulting pentaerythritol esterquat was a mixture of non-ionic pentaerythritol esters and mono-, di-, tris- and tetraquaternary ammonium compounds.

A highly concentrated dispersion of up to 40 weight % active could be made in water without the use of any adjuvants.

| | |
|---|---|
| Softening performance: | ARQUAD ® 2HT |
| REWOQUAT ® W7500 >> | > Example 3 > |
| | WMP – test detergent |
| Biodegradation: | 77% (28 days) |
| Algae toxicity: | >100 ppm |
| Viscosity of dispersions: | 15 mPa · s, 20% active without additives 60 mPa · s, 30% active without additives 1400 mPa · s, 40% active without additives |

EXAMPLE 4

Preparation of bis(H-tallow betaine) ethyleneglycol esterquat 1 mole of ethyleneglycol was esterified with 2 moles of chloroacetic acid at a temperature not exceeding 130° C. The resulting ethyleneglycol ester was then treated with 2 moles of N,N-dimethyl-N-(H-tallow) amine (ARMEEN® DMHTD) in isopropanol under reflux for 2 hours.

The softening performance of this esterquat was found to be the same as that of REWOQUAT® W7500. The product could be dissolved in water, resulting in a clear, viscous aqueous solution containing up to 30% of active material. A 50% active formulation could be made in a 1:1 solution of propylene glycol and isopropanol. The formulation could be dispersed rapidly in cold water without gel particles which might block the dosing compartment of the washing machine being formed.

EXAMPLE 5

Preparation of bis(H-tallowoyl oxyethyl betaine) glycerol esterquat 1 mole of glycerol was esterified with 2 moles of chloroacetic acid at a temperature not exceeding 130° C. The resulting glycerol ester was treated with 2 moles of N,N-dimethyl-N-(H-tallowoyl-oxyethyl) amine in isopropanol under reflux for 2 hours.

The softening performance of this esterquat was as follows:

ARQUAD® 2HT>Example 5>REWOQUAT® W7500>>WMP—test detergent

Algae toxicity: 50 ppm

The product could be dissolved in water, resulting in a clear, viscous aqueous solution containing up to 30% of active material. A 50% active formulation could be made in a 1:1 solution of propylene glycol and isopropanol. The formulation could be dispersed rapidly in cold water without gel particles which might block the dosing compartment of the washing machine being formed.

EXAMPLE 6

Preparation of bis(H-tallowoyl oxyethyl betaine) sorbitol esterquat 1 mole of sorbitol was esterified with 2.1 moles of chloroacetic acid at a temperature not exceeding 130° C. The resulting sorbitol ester was treated with 2.1 moles of N,N-dimethyl-N-(H-tallowoyl-oxyethyl) amine in isopropanol under reflux for 2 hours.

The resulting reaction product displayed the following properties:

Softening performance:

ARQUAD® 2HT>Example 6=REWOQUAT® 7500>>WMP—test detergent

Algae toxicity: 50 ppm

The product could be dissolved in water, resulting in a clear, slightly viscous aqueous solution containing up to 30% of active material. A 50% active formulation could be made in a 1:1 solution of propylene glycol and isopropanol. The formulation could be dispersed rapidly in cold water without gel particles which might block the dosing compartment of the washing machine being formed.

EXAMPLE 7

Preparation of (RA-oyl-oxyethyl betaine) glycerol esterquat 1 mole of glycerol was esterified simultaneously with 2 moles of chloroacetic acid at a temperature not exceeding 130° C. The resulting glycerol ester was subsequently heated under reflux in isopropanol for 2 hours with 2 moles of a product obtained by the transesterification of 1 mole of rapeseed oil and 20 moles of dimethyl aminoethanol (DMAE) for 30 minutes at 140° C. in the presence of 0.5 wt. % KOH as catalyst, followed by the distillation of excess DMAE.

The resulting esterquat could be dissolved in water, resulting in a clear, viscous aqueous solution containing up to 30% of active material. A clear, viscous, 50% active formulation could be made in a 1:1 solution of isopropanol and ethylene glycol/propylene glycol (EG/PG).

EXAMPLE 8

Preparation of bis(tallowoyl oxyethyl betaine) glycerol esterquats 1 mole of glycerol was esterified with 2 moles of chloroacetic acid at a temperature not exceeding 130° C. The resulting glycerol ester was heated under reflux in isopropanol with 2 moles of N,N-dimethyl-N ((partially hydrogenated) tallowoyl-oxyethyl) amine (tallow fatty acid of IV 50) at 80° C. for 2 hours. The resulting quaternary reaction mixture is liquid at room temperature (cloud point (4° C./h): 11° C., non pour point (4° C./h): 10° C.). The resulting esterquat containing 16% isopropanol was mixed with propylene glycol (60% isopropanol containing esterquat/40% propyleneglycol). The cloud point of this composition was 4° C., the non-pour point 3° C. The composition could easily be diluted with water without using any stirring equipment.

EXAMPLE 9

Preparation of bis(tallowoyl oxyethyl betaine) ethylene glycol esterquat 1 mole of ethylene glycol was esterified with 2 moles of chloroacetic acid at a temperature not exceeding 130° C. The resulting ethylene glycol ester was then heated with 2 moles of N,N-dimethyl-N-(tallowoyl-oxyethyl) amine (tallow fatty acid of IV 50) in isopropanol under reflux for 2 hours.

The resulting water-soluble quaternary ammonium compound was well-suited to prepare highly concentrated liquid formulations with low cloud points and low non-pour points. The resulting quaternary reaction mixture containing 17% isopropanol was mixed with propylene glycol (60% isopropanol containing esterquat/40% propylene glycol). The cloud point of this composition was 4° C., the non pour point (cooling rate 4° C./h) 2° C. The product could easily be diluted with water even when the water was cold and agitation was poor.

We claim:

1. A fabric softening composition which comprises at least one biodegradable quaternary ammonium compound of the formula:

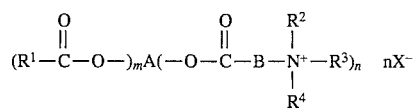

wherein X is an anion, A is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene group containing 1–4 carbon atoms or an alkylidene group containing 2 to 4 carbon atoms, $R^1$, $R^2$, $R^3$ and $R^4$ are independently from each other, straight or branched chain $C_1$–$C_{48}$ alkyl or alkenyl groups, optionally substituted by one or more functional groups which are optionally interrupted by at most 10 ethylene oxide groups, propylene oxide groups, or combinations thereof, or by up to two functional groups selected from

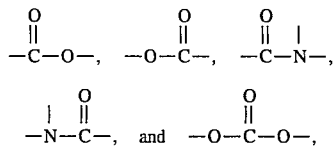

or $R^2$ and $R^3$ may form a ring system containing 5 or 6 atoms in the ring, with the proviso that at least one of said $R^1$, $R^2$, $R^3$, or $R^4$ groups has 22–48 carbon atoms, or at least two of said $R^1$, $R^2$, $R^3$ or $R^4$ groups has 16–20 carbon atoms, or at least three of said $R^1$, $R^2$, $R^3$ or $R^4$ groups has 10–14 carbon atoms.

2. The composition of claim 1, wherein (m+n) is at least 2.

3. The composition of claim 1, wherein said biodegradable quaternary ammonium compound comprises the reaction product of
  a) 1 equivalent of an aliphatic polyol having p hydroxy groups,
  b) m equivalents of an aliphatic carboxylic acid of the formula $R^1$-COOH, and
  c) n equivalents of a $C_{1-4}$ halocarboxylic acid, followed by treatment with
  d) n equivalents of a tertiary amine of the formula $R^2R^3R^4N$ or n equivalents of a secondary amine of the formula $R^2R^3NH$, followed by conversion with n equivalents of a quaternizing agent.

4. The composition of claim 3, wherein the polyol contains 2 to 8 hydroxy groups.

5. The composition of claim 4, wherein the polyol is selected from the group consisting of ethylene glycol, glycerol, pentaerythritol, sorbitol, glucose, saccharose, methyl glucoside, condensed derivatives thereof and mixtures thereof.

6. The composition of claim 4, wherein said polyol is selected from the group consisting of diglycerol, triglycerol, dipentaerythritol and mixtures thereof.

7. The composition of claim 3, wherein the polyol is a natural polyol.

8. The composition of claim 3, wherein the aliphatic acid of the formula $R^1$-COOH is selected from the group consisting of tallow acid, partially hydrogenated tallow acid and mixtures thereof.

9. The composition of claim 3, wherein the $C_{1-4}$ halocarboxylic acid is monochloroacetic acid.

10. The composition of claim 3, wherein the tertiary amine is trimethylamine.

11. The composition of claim 3, wherein the tertiary amine is dimethylethanolamine esterified with a $C_{10-22}$ carboxylic acid.

12. The composition of claim 3, wherein the tertiary amine is dimethylaminopropylamine amidated with a $C_{10-22}$ carboxylic acid.

13. The composition of claim 3, wherein the ester forming derivative of the polyol or the carboxylic acid is a natural fat.

14. The composition of claim 7 wherein said natural polyol is selected from the group consisting of starch, degraded starch, oligomers and polymers containing repeating units of vinyl alcohol and mixtures thereof.

15. The composition of claim 13 wherein said natural fat is a glyceride.

16. A non-aqueous solution which comprises 5 to 90 wt. %, based on the solids content of said solution, of a quaternary ammonium compound of the formula:

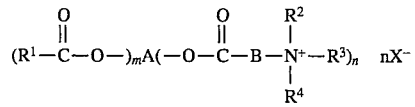

wherein X is an anion, A is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene group containing 1–4 carbon atoms or an alkylidene group containing 2 to 4 carbon atoms, $R^1$, $R^2$, $R^3$ and $R^4$ are independently from each other, straight or branched chain $C_1$–$C_{48}$ alkyl or alkenyl groups, optionally substituted by one or more functional groups which are optionally interrupted by at most 10 ethylene oxide groups, propylene oxide groups, or combinations thereof, or by up to two functional groups selected from

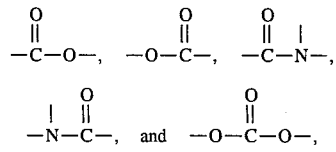

or $R^2$ and $R^3$ may form a ring system containing 5 or 6 atoms in the ring, with the proviso that at least one of said $R^1$, $R^2$, $R^3$ or $R^4$ groups has 22–48 carbon atoms, or at least two of said $R^1$, $R^2$, $R^3$ or $R^4$ groups has 16–20 carbon atoms, or at least three of said $R^1$, $R^2$, $R^3$ or $R^4$ groups has 10–14 carbon atoms.

17. An aqueous solution which comprises 5 to 60 wt. %, based on the solids content of said dispersion, of a quaternary ammonium of the formula:

$$(R^1-\overset{O}{\underset{\|}{C}}-O-)_mA(-O-\overset{O}{\underset{\|}{C}}-B-\overset{R^2}{\underset{R^4}{\underset{|}{N^+}}}-R^3)_n \quad nX^-$$

wherein X is an anion, A is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene group containing 1–4 carbon atoms or an alkylidene group containing 2 to 4 carbon atoms, $R^1$, $R^2$, $R^3$ and $R^4$ are independently from each other, straight or branched chain $C_1$–$C_{48}$ alkyl or alkenyl groups, optionally substituted by one or more functional groups which are optionally interrupted by at most 10 ethylene oxide groups, propylene oxide groups, or combinations thereof, or by up to two functional groups selected from $$-\overset{O}{\underset{\|}{C}}-O-, \quad -O-\overset{O}{\underset{\|}{C}}-, \quad -\overset{O}{\underset{\|}{C}}-\overset{|}{N}-,$$

-continued

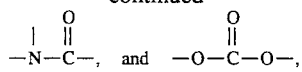

or R² and R³ may form a ring system containing 5 or 6 atoms in the ring, with the proviso that at least one of said R¹, R², R³ or R⁴ groups has 22–48 carbon atoms, or at least two of said R¹, R², R³ or R⁴ groups has 16–20 carbon atoms, or at least three of said R¹, R², R³ or R⁴ groups has 10–14 carbon atoms.

18. The aqueous solution of claim 17 which comprises 5 to 40 wt. %, based on the solids content of said dispersion of said quaternary ammonium compound.

19. A process for preparing biodegradable quaternary ammonium compounds of the formula:

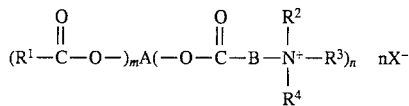

wherein X is an anion, A, is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide, m is 0 or an integer from 1 to p-n, n is an integer from 1 to p-m, and p is an integer of at least 2, B is an alkylene group containing 1–4 carbon atoms or an alkylidene group containing 2 to 4 carbon atoms, R¹, R², R³ and R⁴ are independently from each other, straight or branched chain $C_1$–$C_{48}$ alkyl or alkenyl groups, optionally substituted by one or more functional groups which are optionally interrupted by at most 10 ethylene oxide groups, propylene oxide groups, or combinations thereof, or by up to two functional groups selected from

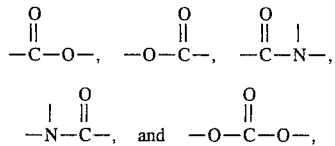

or R² and R³ may form a ring system containing 5 or 6 atoms in the ring, with the proviso that at least one of said R¹, R², R³, or R⁴ groups has 22–48 carbon atoms, or at least two of said R¹, R², R³ or R⁴ groups has 16–20 carbon atoms, or at least three of said R¹, R², R³ or R⁴ groups has 10–14 carbon atoms; wherein said process comprises:

(a) reacting in a first step 1 equivalent of an aliphatic polyol having p hydroxy groups which are optionally esterified, with m equivalents of an aliphatic acid of the formula R¹-COOH or of an ester thereof and n equivalents of a $C_{1-4}$ halocarboxylic acid or of an ester thereof; under reduced pressure at a temperature between 50° and 150° C., followed by either (b) heating with n equivalents of a tertiary amine of the formula R²R³R⁴N, optionally in an organic solvent, at a temperature between 40° and 150° C., or (c) heating with n equivalents of a secondary amine of the formula R²R³NH, optionally in an organic solvent, at a temperature between 40° and 150° C., followed by conversion with n equivalents of a quaternizing agent.

20. The process of claim 19 wherein said quarternizing agent is selected from methylchloride or dimethyl sulphate.

21. The process of claim 19 wherein the temperature of steps b) and c) is between 50° and 100° C.

22. A process for preparing biodegradable quaternary ammonium compounds of the formula:

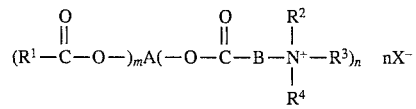

wherein X is an anion, A is an (m+n) valent radical remaining after the removal of (m+n) hydroxy groups from an aliphatic polyol having p hydroxy groups and an atomic ratio of carbon to oxygen in the range of 1.0 to 3.0 and up to 2 groups per hydroxy group selected from ethylene oxide and propylene oxide m is 0 or an integer from 1 to p-n, n is an integer from 1 to p-m, and p is an integer of at least 2, B is an alkylene group containing 1–4 carbon atoms or an alkylidene group containing 2 to 4 carbon atoms, R¹, R², R³ and R⁴ are independently from each other, straight or branched chain $C_1$–$C_{48}$ alkyl or alkenyl groups, optionally substituted by one or more functional groups which are optionally interrupted by at most 10 ethylene oxide groups, propylene oxide groups, or combinations thereof, or by up to two functional groups selected from

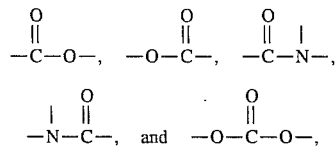

or R² and R³ may form a ring system containing 5 or 6 atoms in the ring, with the proviso that at least one of said R¹, R², R³, or R⁴ groups has 22–48 carbon atoms, or at least two of said R¹, R², R³ or R⁴ groups has 16–20 carbon atoms, or at least three of said R¹, R², R³ or R⁴ groups has 10–14 carbon atoms; wherein said process comprises:

a) reacting in a first step 1 equivalent of an aliphatic polyol having p esterified hydroxy groups with >p moles of dimethyl aminoethanol at a temperature between 80° and 200° C. in the presence of an alkaline catalyst, followed by the distillation of excess dimethyl aminoethanol, in order to obtain a transesterified tertiary amine, b) in a separate second step, esterifying an aliphatic, optionally esterified polyol with at least two moles of chloroacetic acid per mole of polyol, in order to obtain an esterification product followed by c) quaternizing the transesterified tertiary amine obtained in the first reaction step a) with the esterification product of the second reaction step b).

23. The process of claim 22, wherein the optionally esterified polyol used in step b) is a by-product of step a) of the process.

24. The process of claim 22, wherein the aliphatic polyol is glycerol.

* * * * *